(12) United States Patent  (10) Patent No.: US 8,171,825 B1
Adams  (45) Date of Patent: May 8, 2012

(54) MAGNETIC COIL TATTOOING MACHINE

(76) Inventor: James F. Adams, Cape Coral, FL (US)

( * ) Notice: Subject to any disclaimer, the term of this patent is extended or adjusted under 35 U.S.C. 154(b) by 0 days.

(21) Appl. No.: 13/199,163

(22) Filed: Aug. 22, 2011

(51) Int. Cl.
*B43K 5/00* (2006.01)
*H01F 7/08* (2006.01)
(52) U.S. Cl. .......... 81/9.22; 606/185; 606/186; 335/220
(58) Field of Classification Search ................... 81/9.22; 606/183, 185, 186
See application file for complete search history.

(56) References Cited

U.S. PATENT DOCUMENTS

| | | | |
|---|---|---|---|
| 768,413 A | 8/1904 | Wagner | |
| 1,724,812 A | 8/1929 | Waters | |
| 4,159,659 A | 7/1979 | Nightingale | |
| 6,550,356 B1 | 4/2003 | Underwood | |
| 2003/0102945 A1* | 6/2003 | Evans | 335/220 |

* cited by examiner

*Primary Examiner* — Monica Carter
*Assistant Examiner* — Melanie Alexander

(57) ABSTRACT

The present improved magnetic coil tattooing machine incorporates an armature assembly comprising an actuator appendage. The actuator appendage facilitates the actuation of an interrupter switch assembly that is remotely located in relation to the armature assembly. As a result of the described improvements it is now possible to adjust the activation timing of the interrupter switch assembly. An additional and unexpected advantage is a smooth homogenous operation of the interrupter switch assembly rendering the known tuning procedure of prior art obsolete.

1 Claim, 5 Drawing Sheets

MAGNETIC COIL TATTOOING MACHINE

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO SEQUENCE LISTING, A TABLE, OR A COMPUTER PROGRAM LISTING COMPACT DISC APPENDIX

Not applicable.

BACKGROUND OF THE INVENTION

1. Field of the Invention

The present invention relates generally to tattooing, and more particularly to an improved magnetic coil tattooing machine which comprises a new interrupter switch assembly and armature thereby improving operation and providing greater adjustment capability.

2. Description of the Related Art

Magnetic coil tattooing machines known in prior art are shown in the following patents:

| U.S. Pat. No. | U.S. Patents Issue Date | Patentee |
| --- | --- | --- |
| 768,413 | August 1904 | Wagner |
| 1,724,812 | August 1929 | Waters |
| 4,159,659 | July 1979 | Nightingale |
| 6,550,356 | April 2003 | Underwood |

The related art will be discussed in relevance to the present invention.

Referring to FIG. 1 prior art.

The efficiency and usefulness of a magnetic coil tattooing machine is dependent on the machine's ability to oscillate an attached needle assembly $24p$ with a smooth and steady motion. The more homogeneous the motion, the better it will tattoo. Any erratic disturbance or fluctuation of attached needle assembly $24p$ is quite undesirable.

Erratic fluctuation has been an inherent trait of prior art mainly due to a design flaw in an interrupter switch assembly $90p$. Specifically, the problem stems from a contact spring $110p$ being directly mounted on an armature $52p$. Explained thusly, as armature $52p$ completes its upward stroke attached contact spring $110p$ simultaneously closes against a contact screw $21p$ thereby halting the upward travel of armature $52p$. As this occurs, the weight and inertia of armature $52p$ transfers anomalous fluctuations to contact spring $110p$. Consequently, the efficiency of the electrical contact is compromised resulting in an anomalous reciprocation at needle assembly $24p$.

In the past it has been necessary to try and reduce this fluctuation as much as possible by means of a time consuming tuning procedure. This procedure incorporated the repeated trial and error bending of a leaf spring $46p$ in concert with a slight turning in or out of contact screw $21p$. The goal of this procedure was to discover an exact and quite unpredictable amount of spring tension that would adequately compensate for the weight and inertia of armature $52p$. The intricacies of tuning this type of tattooing machine are quite puzzling to many skilled in the art and consequently are difficult to master.

Continuing this discussion, another disappointment found in prior art is the limited adjustability of interrupter switch assembly $90p$ in regard to its activation timing. Further explained, prior art lacks the ability to precisely control at what point interrupter switch assembly $90p$ will be activated during the downward travel of armature $52p$ to coil assembly $70p$ independent of the movement of armature $52p$. This disappointing limit of adjustment inherent in prior art is a result of contact spring $110p$ being directly mounted on armature $52p$. Because of this direct attachment, the downward movement of armature $52p$ predetermines at what instant in time contact spring $110p$ and contact screw $21p$ will separate terminating electrical flow to coil assembly $70p$. Thus it can be understood the marriage of contact spring $110p$ and armature $52p$ is very limiting in versatility of adjustment.

SUMMARY

The present embodiment provides a tattooing machine generally comprised of a frame, at least one magnetic coil, a stroke adjustment assembly, an armature assembly of novel design that includes an attached appendage to facilitate the operation of a unique interrupter switch assembly that is remotely mounted on the embodiment in relation to the armature. One advantage of the present embodiment is that the prerequisite tuning procedure associated with prior art is no longer needed. Another advantage of the present embodiment is to provide a tattooing machine that offers greater and more precise adjustability in regards to the activation timing of the interrupter switch assembly. Still other advantages and benefits of this embodiment will become apparent from the ensuing description and accompanying drawings.

BRIEF DESCRIPTION OF THE DRAWINGS

The present embodiment will now be described with reference to the accompanying drawing figures, in which.

DESCRIPTION OF THE REFERENCED NUMERALS

Figure 1:
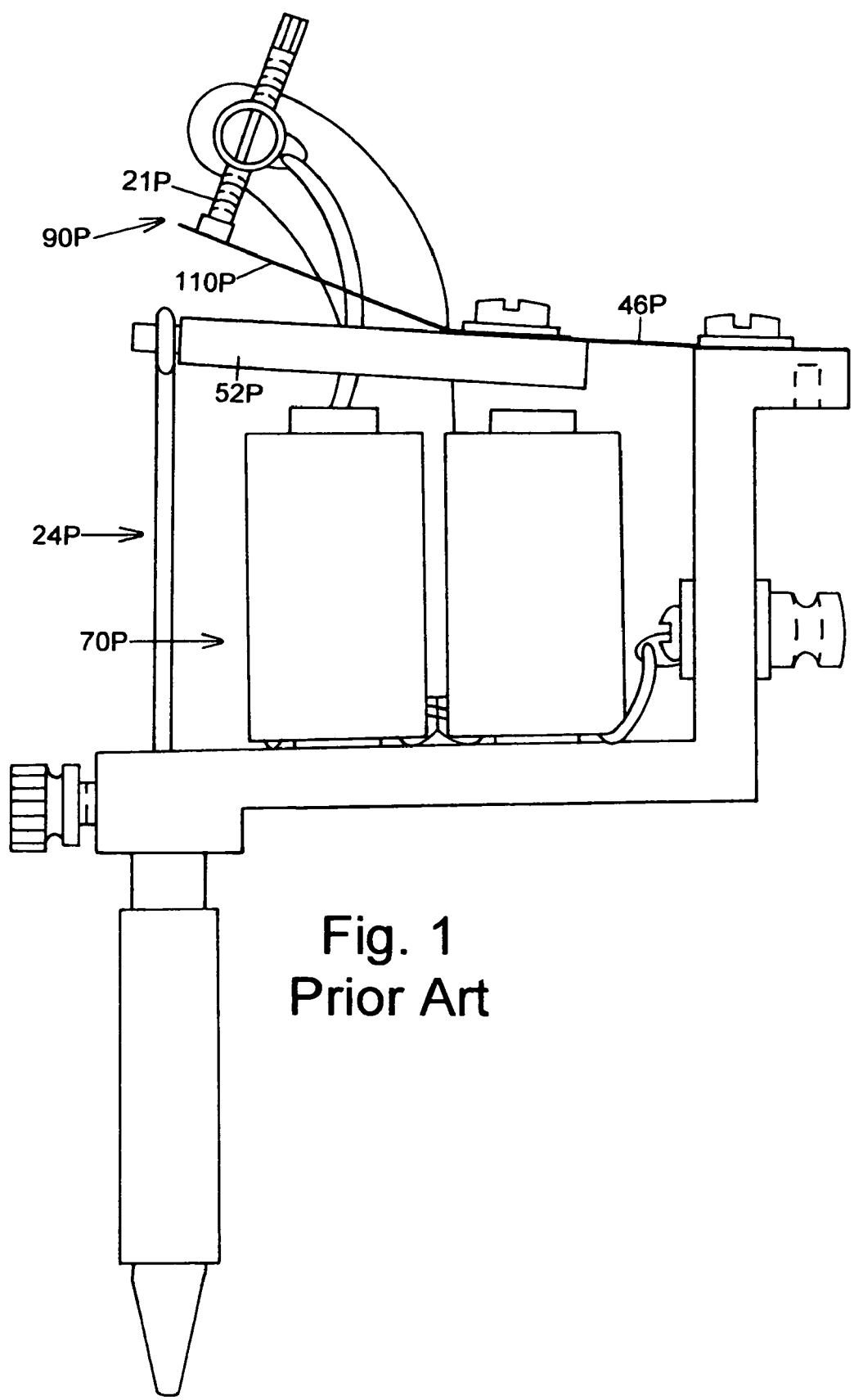
FIG. 1 illustrates an orthogonal view of a generic tattoo machine of prior art.

In reference to the drawings, similar reference characters denote similar elements throughout all the drawings of the present embodiment. The following is a list of the reference characters and associated element:

20 frame assembly
22 needle housing assembly
24 needle assembly
26 tube vice
28 base -continued 30 arm
32 post deck
34 upright
36 mounting tab
38 mounting boss
40 spring deck
42 washer
44 screw
46 leaf spring
48 tapered end
50 armature assembly
52 armature
54 washer
56 screw
58 actuator appendage
60 actuator boot
62 mounting nipple
66 set screw
68 armature pin
70 magnetic coil assembly
72 coil
74 coil core
76 stroke adjustment screw
78 stroke adjustment assembly
80 binding post
82 screw
84 washer
86 thumb screw
88 screw boot
90 interrupter switch assembly
92 insulating washer
94 insulating washer
96 contact strut
98 contact point
100 contact point
102 solder lug
104 insulator sleeve
106 contact spring
108 screw
110 washer
112 jack
114 positive jack terminal
116 nut
118 capacitor
120 capacitor lead
122 capacitor lead
124 coil lead
126 coil lead Description of reference characters and their associated element found in the prior art of FIG. 1:

21p contact screw
24p needle assembly
46p leaf spring
52p armature
70p coil assembly
90p interrupter switch assembly
110p contact spring

DETAILED DESCRIPTION

Figure 2:
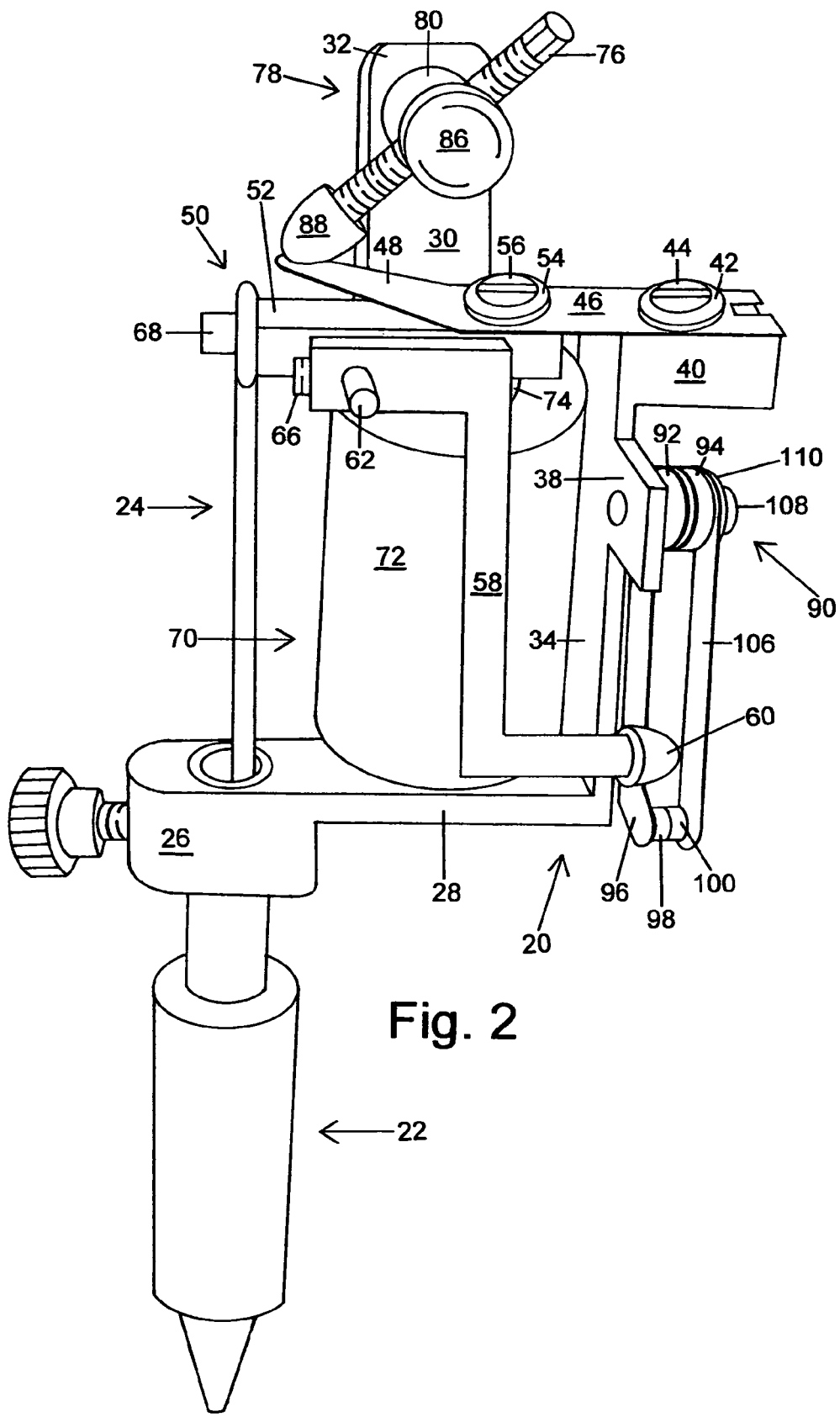
FIG. 2 illustrates a perspective left side view of the present embodiment.
Figure 3:
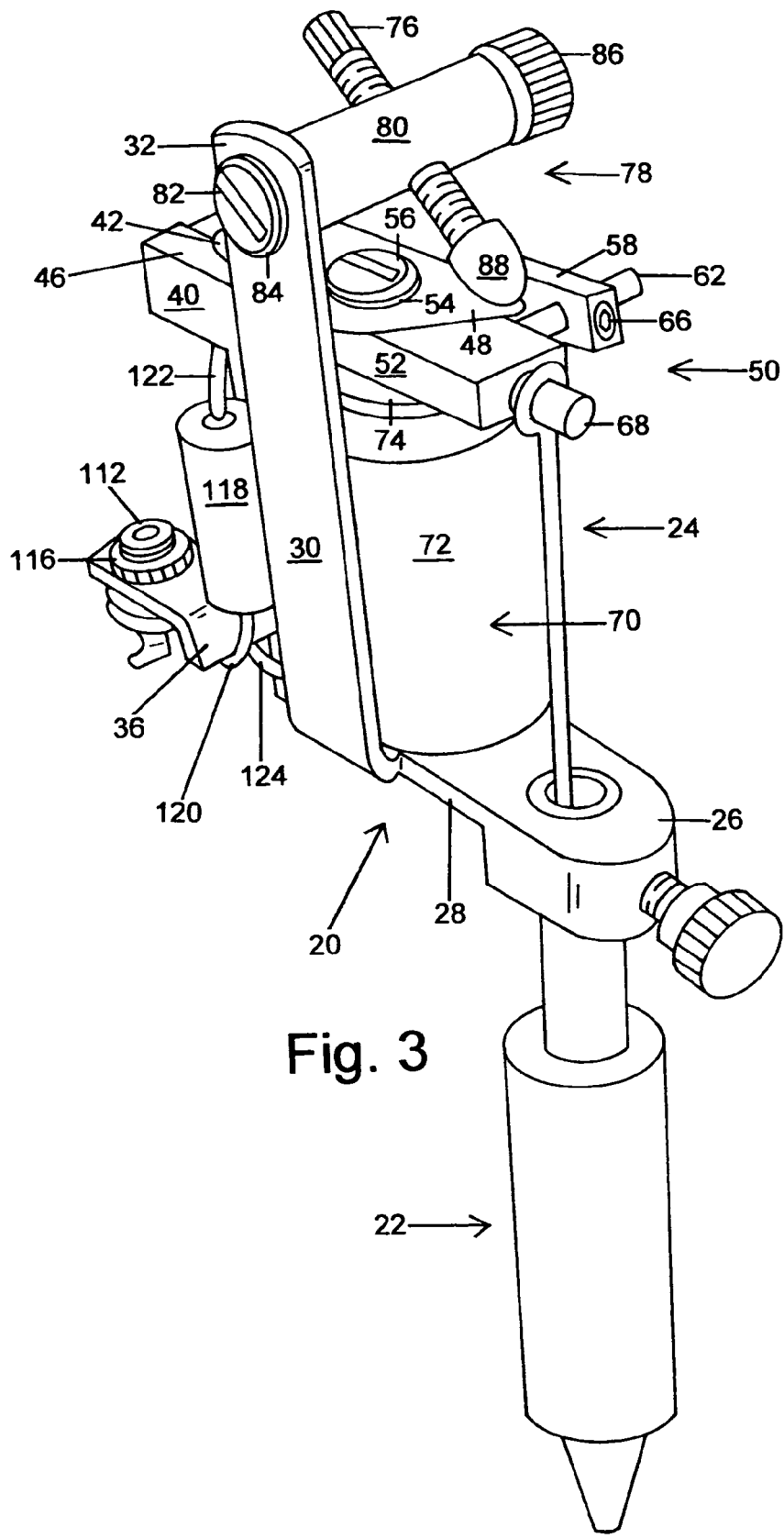
FIG. 3 illustrates a perspective right side view of the present embodiment.
Figure 4:
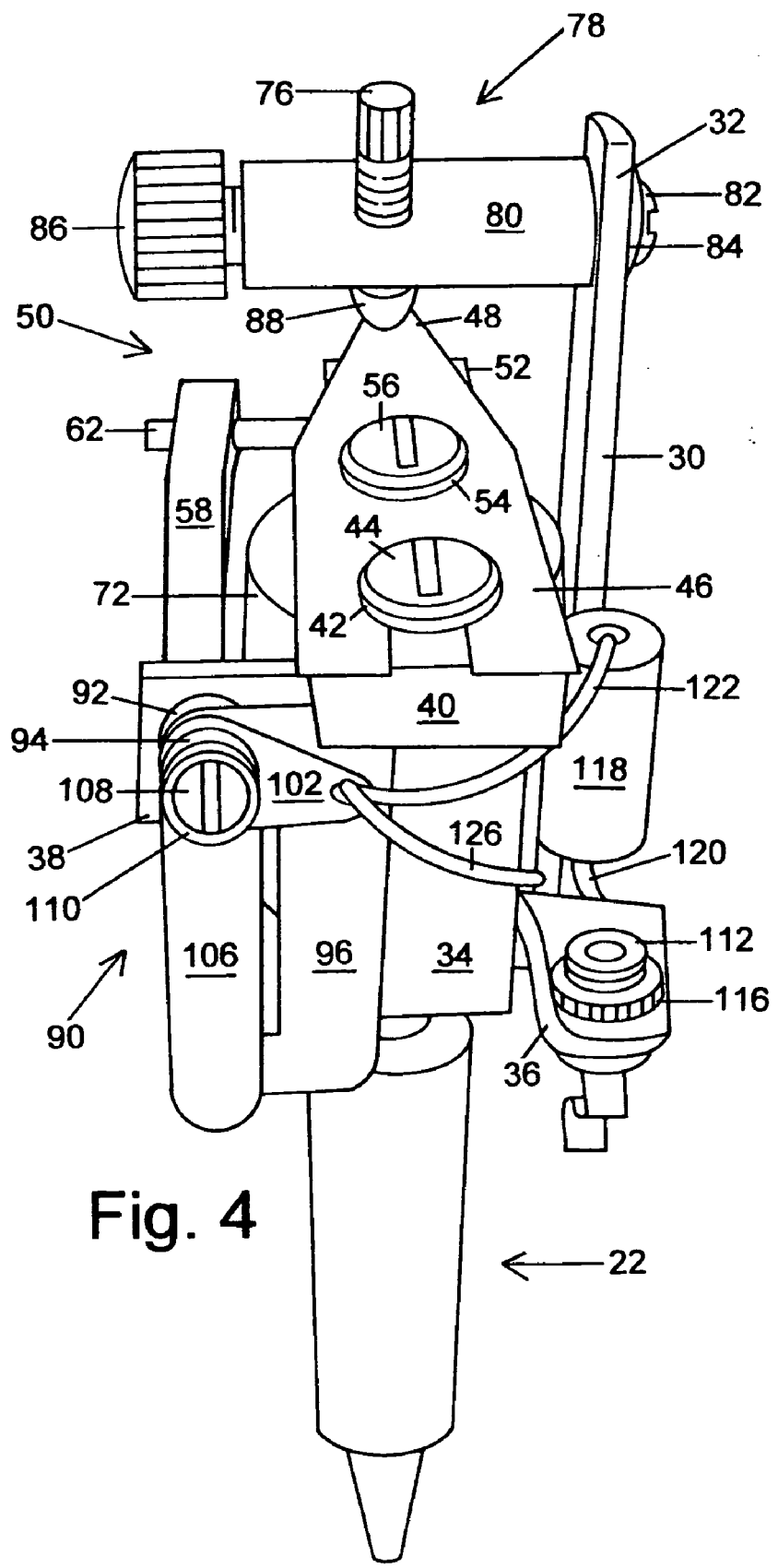
FIG. 4 illustrates a perspective back view (from above) of the present embodiment.

FIGS. 2, 3, and 4 generally illustrate the present embodiment. The major components or sub assemblies of the machine as indicated by arrows are a frame assembly 20, a magnetic coil assembly 70, an armature assembly 50, a stroke adjustment assembly 78, an interrupter switch assembly 90, a needle housing assembly 22, and a needle assembly 24.

Viewing FIG. 2. It should be noted the needle housing assembly 22 as well as the needle assembly 24 are well known to persons skilled in the art as well as being thoroughly discussed in prior art. As of this writing a multitude of pre sterilized and disposable varieties are commercially available. Their detailed description is not a prerequisite to comprehend the improvements of the present embodiment and its teachings. Therefore, a detailed description will not be provided.

Further viewing FIG. 2 it is contemplated at this time frame assembly 20 would best comprise a ferrous metal, for example malleable iron, although other materials could also work. Frame assembly 20 includes a horizontal rectangular base 28 and a rectangular upright 34 which extends vertically from the back end of base 28. Now viewing FIG. 4. Located at the bottom and projecting from the right side of upright 34 is a horizontal flange or mounting tab 36 serving as a mounting foundation for a jack 112. Again viewing FIG. 2, the top end of upright 34 terminates into a rectangular shaped horizontal flange or spring deck 40 serving as a mounting foundation for a leaf spring 46. Projecting from the left side of upright 34 and just below the spring deck 40 is a vertical flange or mounting boss 38 serving as a mounting foundation for interrupter switch assembly 90. The front end of base 28 terminates into a tube vice 26. The exemplary tube vice 26 illustrated herein is one of several available varieties that are well known to persons skilled in the art. Consequently, further explanation is not needed. Best viewed in FIG. 3 projecting from the right side of base 28 and behind tube vice 26 a rectangular arm 30 extends vertically. The top portion of arm 30 is a mounting surface or post deck 32 to facilitate the addition of a binding post 80.

Again viewing FIG. 2, the magnetic coil assembly 70 comprises a magnetic coil 72 attached to base 28 with a screw (not shown) comprised of ferrous steel threaded into the bottom of a coil core 74. It has been presently determined coil 72 would best comprise 10 or 12 layers of AWG 22, 23 or 24 insulated magnet wire. The magnetic coil assembly 70 of this composition and several variations thereof are well known to persons skilled in the art and therefore need not be explained further.

Now viewing FIG. 2, armature assembly 50 comprises an armature 52 manufactured from a ferrous metal such as iron, rectangular in cross section, having a flat end and an opposite end that terminates with a projecting stud or armature pin 68. A mounting nipple 62 fabricated as an integral part of armature 52 projecting horizontally from the left side of armature 52 may be located at any point between the approximate center of armature 52 and the end comprising armature pin 68. Mounting nipple 62 is included to facilitate the mounting of an actuator appendage 58. Actuator appendage 58 can be manufactured from a light weight metal such as but not limited to aluminum and may comprise a variety cross sectional shapes for example round, square or rectangular. Actuator appendage 58, when viewed from the side, may take a variety of shapes. However, it is thought at present the best shape should liberally resemble the letter "z". A mounting hole (not shown) is located near one end of actuator appendage 58 suitably sized to provide a movable fit over mounting nipple 62 allowing for pivotable adjustment of actuator appendage 58. A cushion or actuator boot 60 comprised of a resilient material such as but not limited to rubber or plastic is press fit on the remaining free end of actuator appendage 58 serving as a noise suppressor. The dimensions of actuator appendage 58 need not be exact. A variety of dimensions could suffice providing actuator appendage 58 places actuator boot 60 as close as possible to a contact point 100 during operation. Further comprising actuator appendage 58, a set screw 66 is threaded into the mounted end of actuator appendage 58 for the purpose of fixing actuator appendage 58 in its adjusted position on mounting nipple 62. A leaf spring 46 is attached to the top side of armature 52 at the distal end from armature pin 68 with a metallic screw 56 and a metallic washer 54. Leaf spring 46 includes a tapered end 48. The distal end of leaf spring 46 from tapered end 48 is attached to spring deck 40 with a metallic screw 44 and a metallic washer 42. Leaf spring 46 is constructed from tempered steel in a preferred gage of 0.305 mm. Leaf spring 46 comprises a slight bend to deflect tapered end 48 away from armature 52. This distance need not be specific; however, for example a distance of 5 mm at the farthest point would be adequate.

Now viewing FIG. 3, stoke adjustment assembly 78 comprises a binding post 80 manufactured from a light weight material such as but not limited to plastic or aluminum with a cross sectional shape such as but not limited to round or square. Binding post 80 comprises a threaded hole (not shown) running longitudinally throughout its center. One end of the threaded hole accepts a screw 82 and a washer 84 for the attachment of binding post 80 to post deck 32. At the center of binding post 80 the longitudinal threaded hole is bisected at a right angle by a stroke adjustment screw 76 comprised of a material such as but not limited to aluminum or plastic. The end of the longitudinal threaded hole in binding post 80 that is distal from post deck 32 accepts a thumb screw 86 comprised of a material such as but not limited to aluminum or plastic for the purpose of fixing stroke adjustment screw 76 in its adjusted position. The end of stroke adjustment screw 76 that protrudes from the underside of binding post 80 has a screw boot 88 comprised of material such as but not limited to rubber or plastic press fit over it. Screw boot 88 serving as a noise suppressor.

Figure 5:
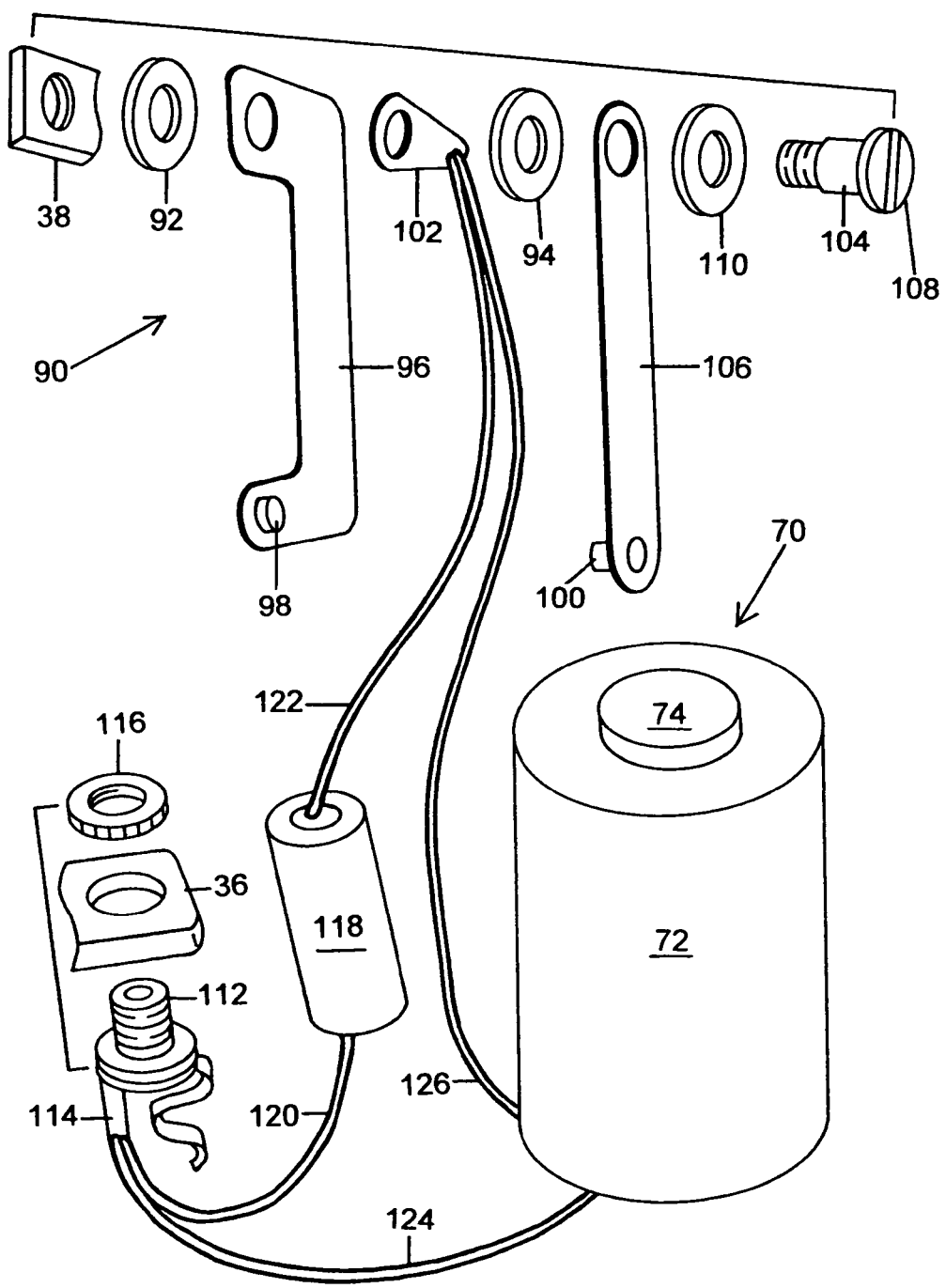
FIG. 5 is a perspective view illustrating the wiring circuit with an exploded view of the interrupter switch assembly in accordance with the present embodiment.

Viewable in FIG. 4 and FIG. 5; however, best viewed in FIG. 5, interrupter switch assembly 90 described in order of assembly comprises an insulating washer 92. Insulating washer 92 is constructed of an electrically non conductive material such as but not limited to vulcanized fibre for the purpose of electrically isolating a contact strut 96 from mounting boss 38. Contact strut 96 includes an attached contact point 98 preferably comprised of but not limited to silver. It is recommended contact strut 96 be comprised of a material that renders it stable and relatively inflexible such as but not limited to steel in an exemplary gauge of 0.635 mm. The preferred shape of contact strut 96 resembles an elongated letter "c" with dimensions approximately 29 mm long and 12 mm wide. However, there are various possibilities to shape and size. A metal solder lug 102 is included to facilitate the soldered attachment of a coil lead 126 and a capacitor lead 122. Solder lug 102 additionally facilitates passage of electrical current from the previously mentioned leads to contact strut 96. An insulating washer 94 provided to electrically isolate solder lug 102 and contact strut 96 from a contact spring 106. Contact spring 106 comprising flexible tempered spring stock preferably but not limited to gage 0.203 mm. It is contemplated at this time the preferred dimensions of contact spring 106 be approximately 29 mm long and 6 mm wide. Contact spring 106 includes an attached contact point 100. Contact point 100 is preferably comprised of but not limited to silver. An insulator sleeve 104 comprised of an electrically non conductive material such as but not limited to thermally shrinkable tubing for the purpose of electrically isolating a screw 108 from contact strut 96 and solder lug 102. Screw 108 passes through insulator sleeve 104, a metallic washer 110, contact spring 106, insulating washer 94, solder lug 102, contact strut 96, and insulating washer 92. Screw 108 then threads into mounting boss 38 thereby fixing interrupter switch assembly 90 to mounting boss 38. The attachment of interrupter switch assembly 90 to mounting boss 38 provides an electrically grounded connection for contact spring 106 of interrupter switch assembly 90.

Now viewing FIG. 4, there are several well known methods to connect DC current to a tattoo machine. All of these methods can be successfully adapted to the present embodiment by a person skilled in the art. However, at present it is suggested that direct current best be connected to the present embodiment by a 3.5 mm mono jack 112 and a matching 3.5 mm mono plug (not shown). Jack 112 is mounted through an appropriately sized hole (not shown) in mounting tab 36 and secured in place by a threaded nut 116 electrically grounding the body of jack 112 to mounting tab 36.

Now viewing FIG. 5, further comprising and completing the electrical circuit is a non polarized axial capacitor 118 having suggested micro ferric value of 100 for the intended purpose of reducing a spark at contact points 98 and 100. Capacitor lead 120 is soldered to positive jack terminal 114. Capacitor lead 122 is soldered to solder lug 102. Coil lead 124 is soldered to positive jack terminal 114. Coil lead 126 is soldered to solder lug 102.

Viewing FIG. 2. When coil 72 is supplied with DC electric current, a magnetic attraction or flux is generated. This magnetic flux extends from coil core 74 across a distance or air gap between coil core 74 and the bottom of armature 52. The magnetic flux attracts iron armature 52 downward to coil core 74. Actuator appendage 58 being affixed to armature 52 by mounting nipple 62 and set screw 66 simultaneously begins a synchronized movement toward contact spring 106. Eventually actuator boot 60, fit over the end of actuator appendage 58, meets contact spring 106 and flexes it back separating contact point 100 from contact point 98. As a result, the flow of electric current supplied to coil 72 is terminated causing a rapid decay of the magnetic flux. Actuator boot 60 suppresses noise that would otherwise be generated by metal to metal contact. Consequently, leaf spring 46 begins returning armature 52 to its upward position. Simultaneously, attached actuator appendage 58 begins to move away from contact spring 106. Eventually the tension in contact spring 106 smoothly returns contact point 100 to contact point 98 thereby restoring current flow to coil 72 allowing the cycle to be repeated. The upward return travel of armature 52 is eventually terminated as the tapered end 48 of attached leaf spring 46 makes contact with screw boot 88, fit over the end of stroke adjustment screw 76. The tapered end 48 of leaf spring 46 acts somewhat as a shock absorber as armature 52 is stopped by stroke adjustment screw 76. Contact point 100 and contact point 98 are allowed to close smoothly and homogenously unaffected by any undesirable influences caused by the weight and inertia of armature 52. This homogenous closure is a direct result of interrupter switch assembly 90 being attached to mounting boss 38 of frame assembly 20, thereby having no direct attachment to armature 52. The homogenous closure of contact point 100 and contact point 98 render the prerequisite "tuning" procedure of prior art obsolete. Stroke adjustment assembly 78 provides a means to adjust the distance of movement or stroke of armature 52 as it is magnetically attracted to coil core 74. The adjustment procedure is as follows. First, leaf spring 46 is bent slightly thereby raising the attached armature 52 to an approximate predetermined distance or air gap above coil core 74. The adjustment is further exacted while the machine is running. Thumb screw 86 is first loosened allowing stroke adjustment screw 76 to be screwed in until screw boot 88, fit over the end of stroke adjustment screw 76, contacts tapered end 48 of leaf spring 46. Screw boot 88 acting as a silencer muffling noise generated by metal to metal contact. Stroke adjustment screw 76 can be screwed in to shorten the stroke length. Stroke adjustment screw 76 can also be unscrewed allowing the stroke length to increase. Finally, thumb screw 86 is retightened securing stroke adjustment screw 76 in its now adjusted position.

According to the improvements of the present embodiment the activation timing of interrupter switch assembly 90 can now be easily adjusted. The procedure is explained as follows. First, set screw 66 is loosened so actuator appendage 58 can be rotated forward or back on mounting nipple 62. This repositioning of the actuator appendage 58 alters the distance between actuator boot 60 and contact spring 106. After the adjustment is accomplished, set screw 66 is retightened fixing the now adjusted actuator appendage 58 in place. The described adjustment being achieved without altering the previously adjusted air gap or distance between armature 52 and coil core 74. The desirable results thereof can be explained as follows: by reducing the distance between actuator boot 60 and contact spring 106, interrupter switch assembly 90 will activate faster. Alternately by increasing the distance between actuator boot 60 and contact spring 106, the interrupter switch assembly 90 will activate slower. For example, it is possible to adjust actuator appendage 58 increasing the distance of actuator boot 60 from contact spring 106 to the point that actuator boot 60 does not activate interrupter switch assembly 90 until the instant just before armature 52 touches coil core 74. As a result, coil 72 can remain energized for a longer duration of the downward travel of armature 52 resulting in a stronger magnetic attraction of armature 52. Alternately, actuator appendage 58 could be adjusted so actuator boot 60 is very close to contact spring 106. The result is an opposite effect whereby interrupter switch assembly 90 activates the instant armature 52 begins to move. Thus, the result is a brief or weaker magnetic attraction. Obviously, there would be additional midrange adjustment capabilities between the two exemplified extremes.

Consequently, the present embodiment offers a previously unknown adjustability in regard to activation timing of the interrupter switch assembly 90. Additionally, it is apparent the present embodiment has the striking advantage of rendering obsolete the "tuning" procedure associated with prior art tattooing machines. While this invention has been described in conjunction with the specific embodiment outlined above, it is evident that many alternatives, modifications and variations will be apparent to those skilled in the art. Accordingly, the present embodiment of the invention as set forth above is intended to be illustrative, not limiting. Various changes may be made without departing from the spirit and scope of the invention.

What is claimed is:

1. An improved electromagnetic tattooing machine comprising: a frame, an armature that includes a means to attach a needle assembly, resilient or pivotal support means for supporting said armature on said frame for oscillation thereon, electromagnet means supported on said frame for oscillating said armature comprising at least one magnetic coil, an electrical circuit for energizing said electromagnet means, an interrupter switch assembly in said electrical circuit for cyclically energizing and de-energizing said electromagnet means in response to the oscillation of said armature, a needle housing assembly comprising an elongated hollow tube having a supported end and a free end, the supported end being attached to said frame, the free end comprising a tip for the support of a needle assembly, said needle assembly comprising a needle or group of needles attached to one end of a needle shaft, the opposite end having a means for attachment to said armature bar for the reciprocation of said needle assembly; the armature comprising an actuator appendage thereby extending the motion of said armature to the interrupter switch assembly thereby activating said interrupter switch assembly; the interrupter switch assembly remotely located in relation to the armature whereby said interrupter switch assembly can be animated by the actuator appendage thereby activating said interrupter switch assembly.

* * * * *